United States Patent
Purdon et al.

(10) Patent No.: US 10,674,956 B2
(45) Date of Patent: Jun. 9, 2020

(54) SYSTEM AND METHOD FOR CHARACTERIZING BRAIN STATES DURING GENERAL ANESTHESIA AND SEDATION USING PHASE-AMPLITUDE MODULATION

(71) Applicant: THE GENERAL HOSPITAL CORPORATION, Boston, MA (US)

(72) Inventors: Patrick L. Purdon, Somerville, MA (US); Eran A. Mukamel, La Jolla, CA (US); Emery N. Brown, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 441 days.

(21) Appl. No.: 15/111,002

(22) PCT Filed: Jan. 14, 2015

(86) PCT No.: PCT/US2015/011304
§ 371 (c)(1),
(2) Date: Jul. 12, 2016

(87) PCT Pub. No.: WO2015/108908
PCT Pub. Date: Jul. 23, 2015

(65) Prior Publication Data
US 2016/0331307 A1 Nov. 17, 2016

Related U.S. Application Data
(60) Provisional application No. 61/927,104, filed on Jan. 14, 2014.

(51) Int. Cl.
*A61B 5/00* (2006.01)
*A61B 5/04* (2006.01)
(Continued)

(52) U.S. Cl.
CPC .......... *A61B 5/4821* (2013.01); *A61B 5/048* (2013.01); *A61B 5/04015* (2013.01);
(Continued)

(58) Field of Classification Search
None
See application file for complete search history.

(56) References Cited

U.S. PATENT DOCUMENTS

2003/0088161 A1 5/2003 Stengel et al.
2007/0179391 A1 8/2007 Kurtz et al.
2013/0197339 A1 8/2013 Bardakjian et al.

FOREIGN PATENT DOCUMENTS

WO WO2012154701 A1 11/2012

OTHER PUBLICATIONS

Purdon et al., Electroencephalogram signatures of loss and recovery of consciousness from propofol. PNAS E1142-E1151. Mar. 4, 2013, retrieved Mar. 18, 2015 from Internet URL: http://www.pnas.org/content/11012/E1142.full.pdf.
(Continued)

*Primary Examiner* — Etsub D Berhanu
(74) *Attorney, Agent, or Firm* — Quarles & Brady LLP (57) ABSTRACT

A system and method for monitoring and/or controlling a state of consciousness of a subject experiencing anesthesia are provided. In some aspects, the system includes a plurality of sensors placed about the subject and configured to acquire electroencephalogram ("EEG"} data therefrom while the subject is receiving anesthesia, and at least one processor configured to receive the EEG data from the plurality of sensors, and perform a phase-amplitude coupling analysis using the received EEG data to determine a phase-amplitude frequency distribution. The at least one processor is also configured to identify a state of consciousness of the subject using the determined phase-amplitude
(Continued)

frequency distribution, and generate a report indicative of the state of consciousness of the subject.

7 Claims, 11 Drawing Sheets

(51) Int. Cl.
*A61B 5/0478* (2006.01)
*A61B 5/048* (2006.01)

(52) U.S. Cl.
CPC .......... *A61B 5/0478* (2013.01); *A61B 5/4839* (2013.01); *A61B 5/7246* (2013.01); *A61B 5/742* (2013.01)

(56) References Cited

OTHER PUBLICATIONS

International Search Report and Written Opinion for PCT/US2015/011304, dated May 6, 2015.

SYSTEM AND METHOD FOR CHARACTERIZING BRAIN STATES DURING GENERAL ANESTHESIA AND SEDATION USING PHASE-AMPLITUDE MODULATION

CROSS-REFERENCE TO RELATED APPLICATIONS

This application represents the national stage entry of PCT International Application No. PCT/US2015/011304 filed Jan. 14, 2015, which is based on, and claims priority to U.S. Provisional Application Ser. No. 61/927,104, filed Jan. 14, 2014, both of which are incorporated herein by reference in their entirety for all purposes.

BACKGROUND OF THE INVENTION

The present disclosure generally relates to systems and method for monitoring a state of a subject and, more particularly, to systems and methods for appropriate monitoring and controlling states of a subject receiving a dose of anesthetic compound(s) or, more colloquially, receiving a dose of "anesthesia" or sedation.

Although the molecular actions of many anesthetic drugs at specific receptors are known, alterations in network dynamics that disrupt information processing and produce unconsciousness have remained elusive. Typically, loss of consciousness is accompanied by increased electroencephalogram ("EEG") power across a broad range of frequencies less than 40 Hz. Traditional analyses, including visual interpretation of EEG traces and time-frequency power spectral analysis, are computationally simple and play a central role in neurophysiology and clinical EEG applications. However, power spectral analysis treats the EEG as a collection of independent frequency bands, offering limited insight into the modulation of network activity as a whole. Because cortical networks frequently express oscillations in multiple frequency bands simultaneously, nonlinear biophysical processes, such as neuronal spiking, induce cross-frequency coupling, which is undetectable by spectral analysis. Identifying global brain states, such as sleep stages or general anesthesia-induced unconsciousness, remains a significant challenge for understanding cortical dynamics. Moreover, an EEG-based framework for understanding brain state transitions during general anesthesia will be critical for improving subject monitoring to avoid complications, such as intra-operative awareness.

Given the above, there remains a need for systems and methods that accurately characterize brain states of subjects subjected to anesthesia or sedation.

SUMMARY OF THE INVENTION

The present disclosure provides systems and methods directed to monitoring and controlling subjects using acquired physiological data, for use in certain medical procedures, such as general anesthesia and sedation. Specifically, the present invention provides systems and methods.

In accordance with one aspect of the disclosure, a system for monitoring and/or controlling a state of consciousness of a subject experiencing anesthesia are provided. The system includes a plurality of sensors placed about the subject and configured to acquire electroencephalogram ("EEG") data therefrom while the subject is receiving anesthesia, and at least one processor configured to receive the EEG data from the plurality of sensors, and perform a phase-amplitude coupling analysis using the received EEG data to determine a phase-amplitude frequency distribution. The at least one processor is also configured to identify a state of consciousness of the subject using the determined phase-amplitude frequency distribution, and generate a report indicative of the state of consciousness of the subject.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The present invention will hereafter be described with reference to the accompanying drawings, wherein like reference numerals denote like elements.

DETAILED DESCRIPTION

Rhythmic oscillations shape cortical dynamics during active behavior, sleep, and general anesthesia. Among other signatures, cross-frequency phase-amplitude coupling is a prominent feature of cortical oscillations, but its role in organizing conscious and unconscious brain states is poorly understood. Using high-density EEG and intracranial electrocorticography during gradual induction of propofol general anesthesia in humans, the present disclosure describes results from rapid drug-induced transitions between distinct states with distinct phase-amplitude coupling and cortical source distributions. These distinct states of phase-amplitude coupling reflect different states of arousal or consciousness. These results, provide objective electrophysiological landmarks of distinct unconscious brain states, and could be used to help improve EEG-based monitoring during general anesthesia and sedation, as will be described.

In particular, the present disclosure recognizes that information necessary for accurately identifying and characterizing distinct global brain states may be contained in patterns of coupling between distinct frequency bands. Thus, systems and methods are provided herein that implement such information, and other information, for purposes of monitoring and controlling a subject during administration of anesthesia or sedation.

In particular, one form of cross-frequency interaction is phase-amplitude coupling, in which power within one frequency band waxes and wanes at specific phases of an underlying, lower-frequency rhythm. Phase-amplitude coupling is widespread during sleep, waking, and general anesthesia, and has been related to attention and behavior in human and primate cortex. In previous work by the inventors using scalp EEG recordings during propofol-induced general anesthesia, two forms of coupling were discovered between the phase of low-frequency activity ("LFA"), which is typically in a frequency range roughly between 0.1 to 2 Hz, and the amplitude of rhythms in a frequency range roughly between 8 and 14 Hz. In particular, one form of coupling can occur during the transitions to and from an unconscious state, herein referred to as "trough-max", whereas another can occur at deep levels of unconsciousness, herein referred to as "peak-max." The cortical networks involved in these distinct modulation patterns, their frequency dependence, and their relationship to other brain states, such as burst suppression, are presently unclear.

Therefore, results from investigations of cortical generators of such modulation patterns are presented herein using source localization analyses and intracranial electrocorticography. In addition, analysis of their frequency dependence is performed, demonstrating effects on individual subjects, and clarifying their relationship to burst suppression. In particular, findings show that patterns of cross-frequency coupling reflect dynamics within distinct cortical networks and identify transitions in global brain states.

Figure 1A:
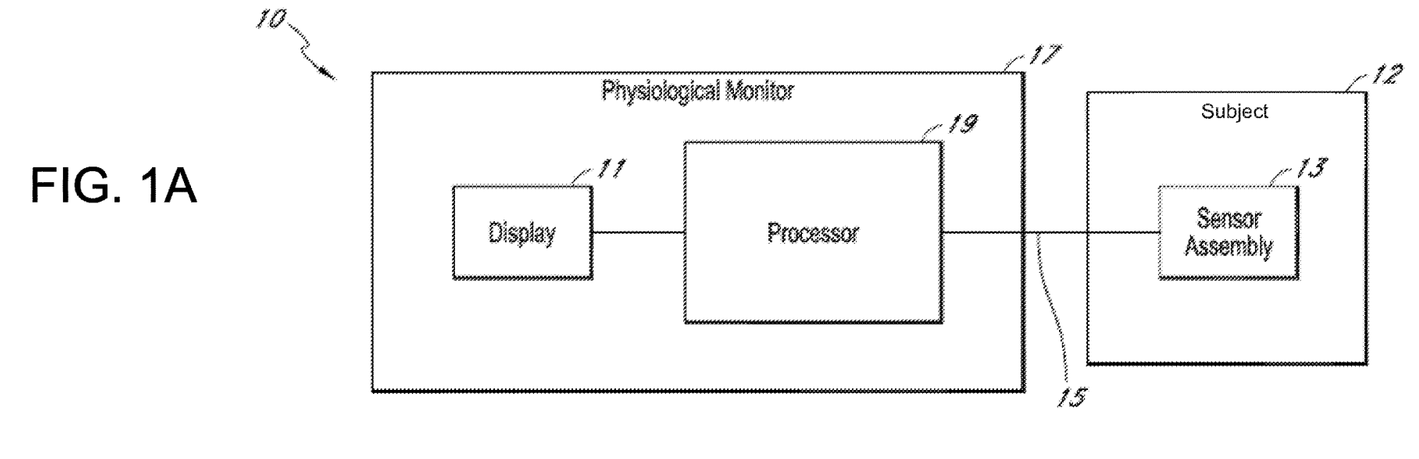
FIG. 1A is schematic block diagram of an example physiological monitoring system, in accordance with aspects of the present disclosure.
Figure 1B:
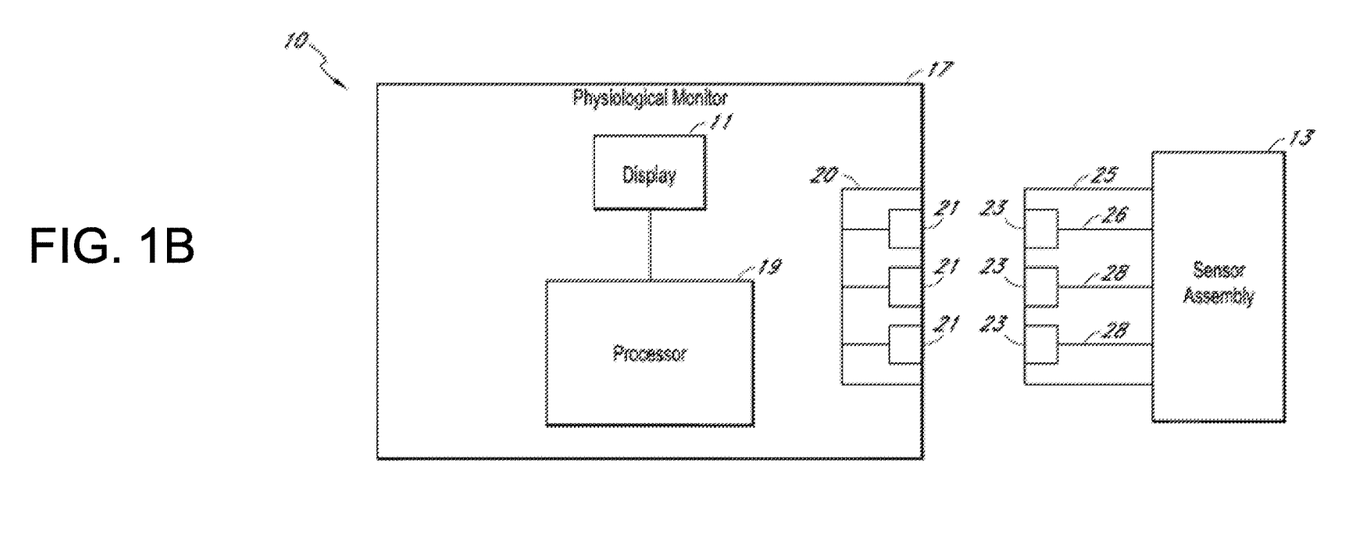
FIG. 1B is schematic block diagram of another example physiological monitoring systems, in accordance with aspects of the present disclosure.

Referring now to the drawings, FIGS. 1A and 1B illustrate example subject monitoring systems and sensors that can be used to provide monitoring of a subject, for instance, during administration anesthesia, sedation, or other medical procedure.

For example, FIG. 1A shows an embodiment of a monitoring system 10. Specifically, using monitoring system 10, a subject 12 is monitored using a sensor assembly 13 included therein, which can transmit various signals over a cable 15 or other communication link or medium to a physiological monitor 17. The physiological monitor 17 includes a processor 19 and, optionally, a display 11 for reporting a variety of information, such as information related to the condition of the subject 12, state of consciousness or transitions from states of consciousness of the subject 12, as well as other states of the subject 12. In some designs, the monitoring system 10 may be a portable monitoring system. In other designs, the monitoring system 10 may be a pod without a display, and adapted to provide physiological parameter data to a display.

The sensor assembly 13 can include one or more sensing elements such as, for example, electrical EEG sensors, or the like. The sensor assembly 13 can generate respective signals by measuring physiological parameters of the subject 12. The signals are then processed by one or more processors 19. The one or more processors 19 then communicate the processed signal to the display 11, if provided, or other logically connected output. In an embodiment, the display 11 is incorporated in the physiological monitor 17. In another embodiment, the display 11 is separate from the physiological monitor 17.

For clarity, a single block is used to illustrate the sensor assembly 13 shown in FIG. 1A. However, it should be understood that the sensor assembly 13 shown is intended to represent one or more sensors configured for placement at a variety of locations about the skull of the subject 12 and acquire various physiological signals. In one embodiment, the sensor assembly 13 can include sensors of one type, such as EEG sensor. In other embodiments, the sensor assembly 13 can include multiple types of sensors, such as EEG sensors, brain oxygenation sensors, optical sensors, galvanic skin response sensors, and so on. In each of the foregoing embodiments, additional sensors of different types are also optionally included. Other combinations of numbers and types of sensors are also suitable for use with the monitoring system 10.

In some embodiments of the system shown in FIG. 1A, all of the hardware used to receive and process signals from the sensors are housed within the same housing. In other embodiments, some of the hardware used to receive and process signals is housed within a separate housing. In addition, the physiological monitor 17 of certain embodiments includes hardware, software, or both hardware and software, whether in one housing or multiple housings, used to receive and process the signals transmitted by the sensor assembly 13.

As shown in FIG. 1B, the sensor assembly 13 can include a cable 25. The cable 25 can include three conductors, for example, within an electrical shielding. One conductor 26 can provide power to a physiological monitor 17, one conductor 28 can provide a ground signal to the physiological monitor 17, and one conductor 28 can transmit signals from one sensor in the sensor assembly 13 to the physiological monitor 17. For multiple sensors, one or more additional cables 25 can be provided.

In some embodiments, the ground signal is an earth ground, but in other embodiments, the ground signal is a subject ground, sometimes referred to as a subject reference, a subject reference signal, a return, or a subject return. In some embodiments, the cable 25 carries two conductors within an electrical shielding layer, and the shielding layer acts as the ground conductor. Electrical interfaces 23 in the cable 25 can enable the cable to electrically connect to electrical interfaces 21 in a connector 20 of the physiological monitor 17. In another embodiment, the sensor 13 and the physiological monitor 17 communicate wirelessly.

Processor 19 may be configured to perform a number of steps for processing and analyzing data received from the sensor assembly 13. In particular, process 19 can be configured to assemble the data in any number of forms, including waveforms, spectrograms, coherograms, modulograms, and so on. Also, processor 19 can perform a phase-amplitude coupling analysis to determine a phase-amplitude coupling frequency distribution, and/or a phase-amplitude coupling spatial distribution, in accordance with the present disclosure. Additionally, processor 19 may also be configured to identify other signal markers or signatures associated with the received the data using various analysis methods, including waveform analyses, spectral analyses, frequency analyses, coherence analyses and so on. For example, signal markers or signatures can include various signal amplitudes, phases, frequencies, power spectra, frequency distributions, spatial distribution, and so forth.

In some configurations, systems shown in FIGS. 1A and 1B may further include a memory, database or other data storage locations (not shown), accessible by processor 19, to include reference information or other data. Specifically, such reference information can include reference listings or look-up tables including signals, signal markers or signatures associated with specific anesthetic drugs, treatments conditions, and the like. In some aspects, such reference information can be used by the processor 19, optionally including user input or selections, to identify states of consciousness of a subject. In particular, processor 19 may process and analyze acquired data to determine signal markers, signatures or patterns, including phase-amplitude coupling frequency patterns, spatial distribution patterns, phase-amplitude modulation polarity patterns, and so on. Subsequently, subject states of consciousness may be identified by performing a comparison of the determined signal markers, signatures or patterns with those categorized in the reference.

In other aspects, processor 19 may identify states of consciousness of a subject by acquiring and/or processing baseline data, such as baseline phase-amplitude frequency distribution data, a baseline polarity of the phase-amplitude modulation, and so on. States of consciousness may then be identified by processor 19 by performing a comparison of the baseline data to the data received from the sensor assembly 13, for instance, while undergoing a medical procedure, such as receiving anesthesia or sedation.

Figure 2:
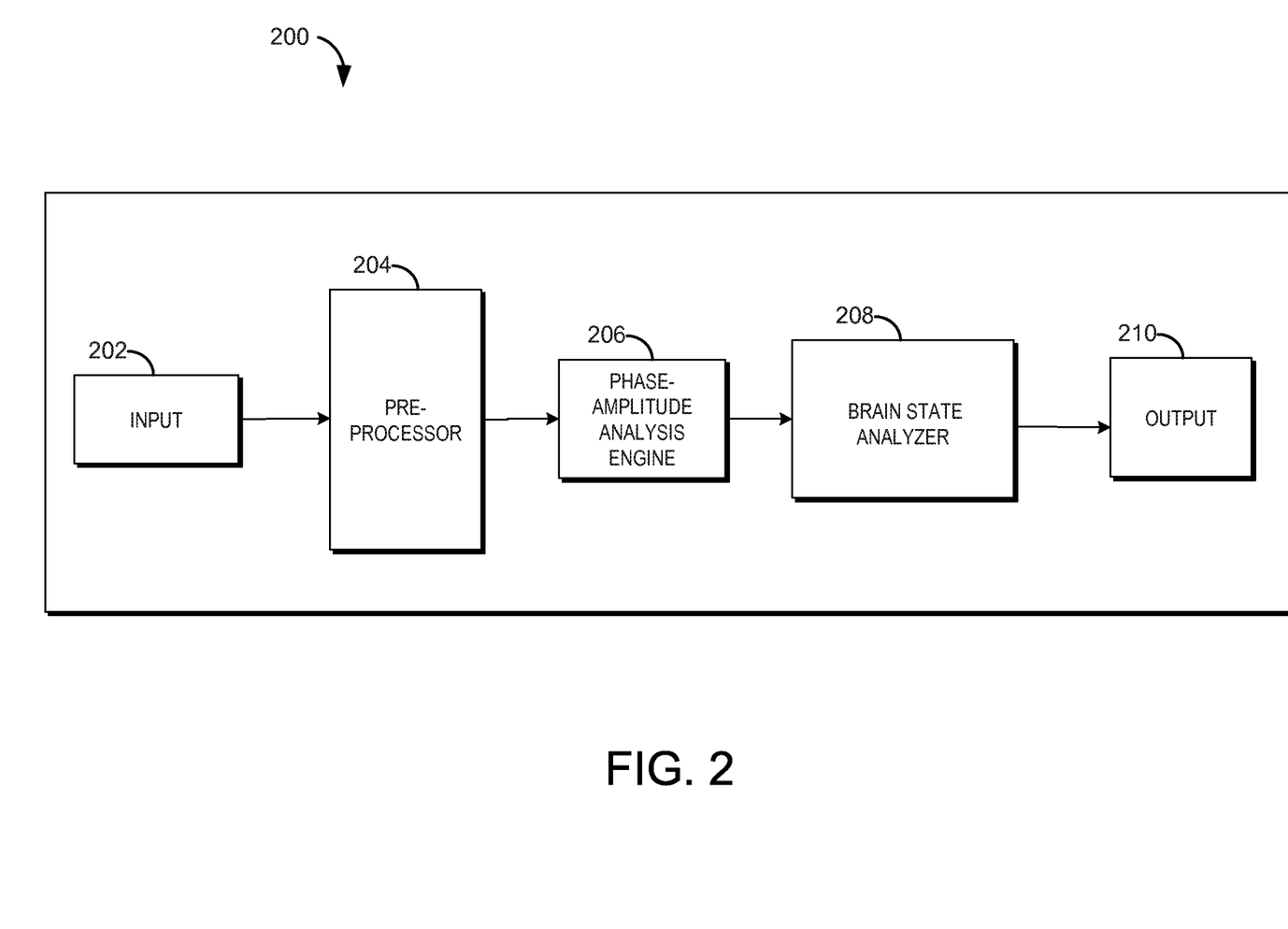
FIG. 2 is an illustration of an example system for use in accordance with the present disclosure.

Referring to FIG. 2, an example system 200 for use in carrying out steps associated with identifying or characterizing states of a subject, in accordance with the present disclosure, is illustrated. The system 200 includes an input 202, a pre-processor 204, a phase-amplitude analysis engine 206, a state analyzer 208, and an output 210. Some or all of the modules of the system 200 can be implemented by a patient monitor as described above with respect to FIG. 1.

The pre-processor 204 may be designed to carry out any number of processing steps for operation of the system 200. In addition, the pre-processor 204 may be configured to receive and pre-process data received from the input 202. In some aspects, pre-processor 204 may be configured to assemble the received data into in any number of forms, including time series waveforms. In addition, the pre-processor 204 may be configured to perform any desirable noise rejection to filter any interfering signals associated with the data, as well as well as select components, for example, frequency components, associated with the data.

In some aspects, the pre-processor 204 may also be configured to receive an indication via the input 202, such as information related to administration of an anesthesia compound or compounds, and/or an indication related to a particular subject profile, such as a subject's age, height, weight, gender, or the like, as well as drug administration information, such as timing, dose, rate, and the like.

In addition to the pre-processor 204, the system 200 may further include a phase-amplitude analysis engine 206, in communication with the pre-processor 202, designed to receive pre-processed data from the pre-processor 202 and carry out steps necessary for a phase-amplitude analysis, in accordance with aspects of the present disclosure, as well as other analyses. In some aspects, may be configured to assemble modulograms, spectrograms, coherograms, and so on, using data received from the pre-processor 206.

As a result, the phase-amplitude analysis engine 206 may provide data related to phase-amplitude frequency distributions, polarity of a phase-coupling modulation, spatial distribution of phase-amplitude modulation, and so on, which may then be used by the brain state analyzer 208 to determine brain state(s) of the subject. For example, the brain state analyzer 208 may identify states of consciousness or sedation during administration of a drug with anesthetic properties, such as a loss of consciousness, a recovery from consciousness, or a level of consciousness, as well as confidence indications related to the determined state(s). In some aspects, the brain state analyzer 208 may utilize reference or baseline data, as described, in determining brain state(s) of the subject.

Information related to the determined state(s) may then be relayed to the output 210, along with any other desired information, in any shape or form, intermittently or in real-time. In some aspects, the output 210 may include a display configured to provide information or indicators with respect to denoised spectral decompositions, that may be formulated using spectrogram representations, either intermittently or in real time.

Figure 3:
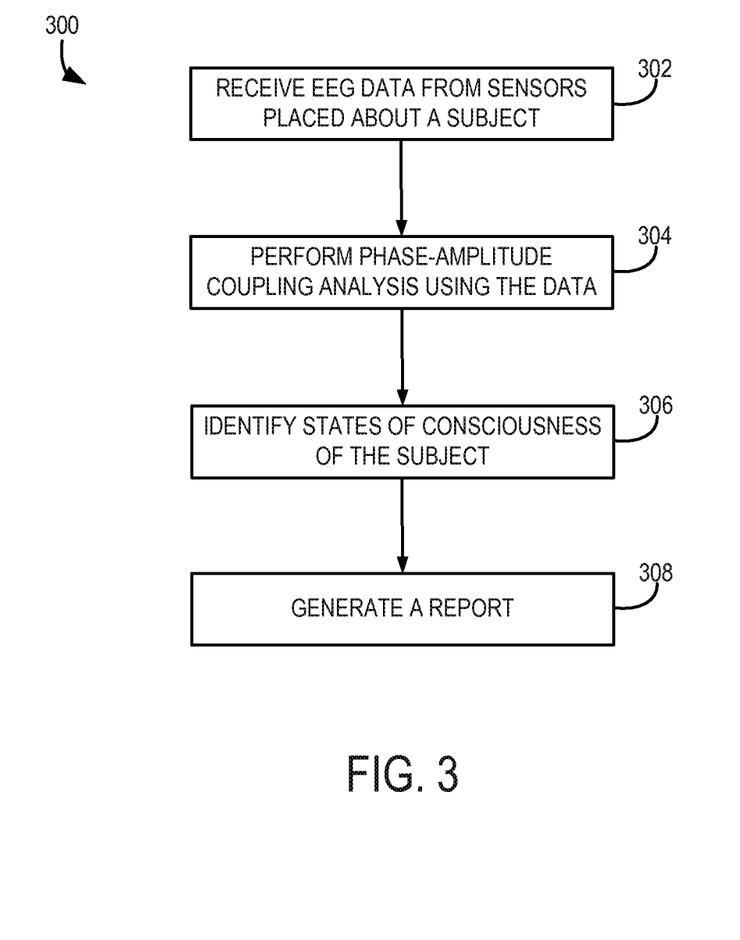
FIG. 3 is a flowchart illustrating the steps in a process, in accordance with the present disclosure.

Turning now to FIG. 3, a process 300 in accordance with aspects of the present disclosure is shown. Beginning with process block 302, any amount of physiological data may be obtained, including EEG data acquired from various locations about a subject's skull using, for example, using systems described with respect to FIGS. 1A and 1B. In some aspects, the physiological data may include baseline data.

Then at process block 304, a phase-amplitude coupling analysis, along with other analyses, may be performed using the received data. In particular, a number of phase-amplitude modulograms $M(t, \varphi)$ may be constructed, as detailed below, which characterize the relative amplitude of activity in a frequency band $f_{amp}$, as a function of the phase of the rhythm in band $f_{ph}$. This can include processing received EEG signals, $x(t)$, by applying a band-pass filter to extract each frequency band of interest, $x_b(t)$, where b refers to the amplitude frequency band or phase frequency band. Preferably, filters may chosen to adequately isolate these frequency bands while allowing temporal resolution of changes in phase-amplitude coupling, which occur within about 2 min or less. A symmetric finite impulse response filters may be used using a least-squares approach. For example, using a MATLAB function firls; $f_{ph}$ passband=0.1-1 Hz, transition bands=0.085-0.1 and 1-1.15 Hz, attenuation in stop band dB, filter order 2207; $f_{amp}$, passband=8-13.9 Hz, transition bands=5.9-8.0 and 13.9-16.0 Hz, attenuation in stop band dB, filter order 513. However, it may be appreciated that other frequencies filters, and other processing parameters may be utilized. A Hilbert transform may then be used to extract the instantaneous amplitude and phase.

Specifically a modulogram may be computed by assigning a given temporal sample to one of, say, N=18 equally spaced phase bins based on the instantaneous value of $\psi_{ph}(t)$, although other values are possible, and then averaging the corresponding values of $A_{amp}(t)$ within say a 2 min epoch as follows:

$$M(t, \phi) = \frac{\int_{t-\frac{\delta t}{2}}^{t+\frac{\delta t}{2}} \int_{\phi-\frac{\delta\phi}{2}}^{\phi+\frac{\delta\phi}{2}} A_{amp}(t')\delta(\psi_{ph}(t') - \phi')d\phi' \, dt'}{\int_{t-\frac{\delta t}{2}}^{t+\frac{\delta t}{2}} A_{amp}(t')dt'}; \quad (1)$$

where $\delta=120$ s and $\delta\varphi=2\pi/N$. Note that $$\sum_{n=1}^{N} M(t, \phi_n) = 1, \phi_n = 2\pi n/N,$$

so that M(t, φ) is normalized over phase bins. To reduce noise in estimated modulagrams, the value of M(t, φ) may be averaged from multiple electrode locations. For example, six frontal electrodes Fz in the standard montages may be averaged.

A modulation index, MI(t) may be defined as follows:

$$MI(t) = \sum_{n=1}^{N} M(t, \phi_n)\log_2 \frac{M(t, \phi_n)}{1/N}. \quad (2)$$

A statistical significance may be assessed by performing a permutation test. For instance, a number of random time shifts, Δt, may be sampled from a uniform distribution on an interval, for example, between −60 sec and +60 sec. The value for $MI_{perm}(t)$ may then be computed using the original phase, $\psi_{ph}(t)$, and the shifted amplitude, $A_{amp}(t-\Delta t)$. MI(t) may then be deemed significant if it exceeding, for instance, 95% of the permuted values, $MI_{perm}(t)$. A bootstrap calculation could also be performed to assess statistical significance or compute confidence intervals.

In case of significant coupling, a phase of the frequency band $f_{ph}$ at which the amplitude of the frequency band $f_{amp}$ is greatest can be determined by finding the phase of the sinusoid that best fit the modulogram at each time point as follows:

$$\Phi(t) \equiv \arg\left[\sum_{n=1}^{N} e^{i\phi_n} M(t, \phi_n)\right]. \quad (3)$$

In some aspects, an analysis of a spatial distribution of phase-amplitude coupling may also be performed at process block 204 using data obtained from multiple sensor locations about the subject's head. In particular, a scalp topography of phase-amplitude coupling and EEG power may be performed, generating scalp patterns or maps. In some aspects, combined maps across multiple subjects may be produced, for example, by taking a median of the population data.

To estimate the spatial distribution of cortical currents responsible for peak- and trough-max EEG coupling, for instance, a source localization analysis of the EEG signal may be performed using the minimum norm estimate (MNE) followed by phase-amplitude coupling analysis of the estimated cortical current sources. For instance, Freesurfer software may be used to reconstruct tissue surfaces for the forward model based on high-resolution structural images, for example, obtainable using a magnetic resonance imaging system. A three layer boundary element forward model may be constructed using MNE software.

Localization analysis may use a reduced-dimension source space of say 1284 patches of uniform current density, each for example, 1.25 cm in diameter, although other values may be possible. Source current time series estimated by MNE may then be used to calculate the MI, as described above. In some aspects, to test significance within each patch, phase and amplitude may be resampled from within each subject's trough- or peak-max epoch to construct a null distribution for the MI. In some aspects, these may be combined across a number of subjects using surface-based registration to obtain an average cortical surface map. A p-value for each patch was may be obtained by fitting a γ distribution to the group average null distribution; validity of the γ distribution may be confirmed using Pearson's $\chi^2$ test (for instance, at 95% confidence level). The p-values may be used to control the false discovery rate.

Referring again to FIG. 3, at process block 306, states of consciousness of the subject may then be identified using information obtained from analyses performed at process block 304. For instance, determined information at process block 306 may include phase-amplitude frequency distributions, polarity of a phase-coupling modulation, spatial distribution of phase-amplitude modulation, and so on.

Then at process block 308 a report may be generated, for example, in the form a printed report or, preferably, a real-time display. The report may include raw or processed data, signature information, r indications related to current or future brain states or levels of consciousness. Displayed signature information or determined states may be in the form of waveforms, spectrograms, coherograms, modulograms, probability curves, maps, indices and so forth.

Figure 4:
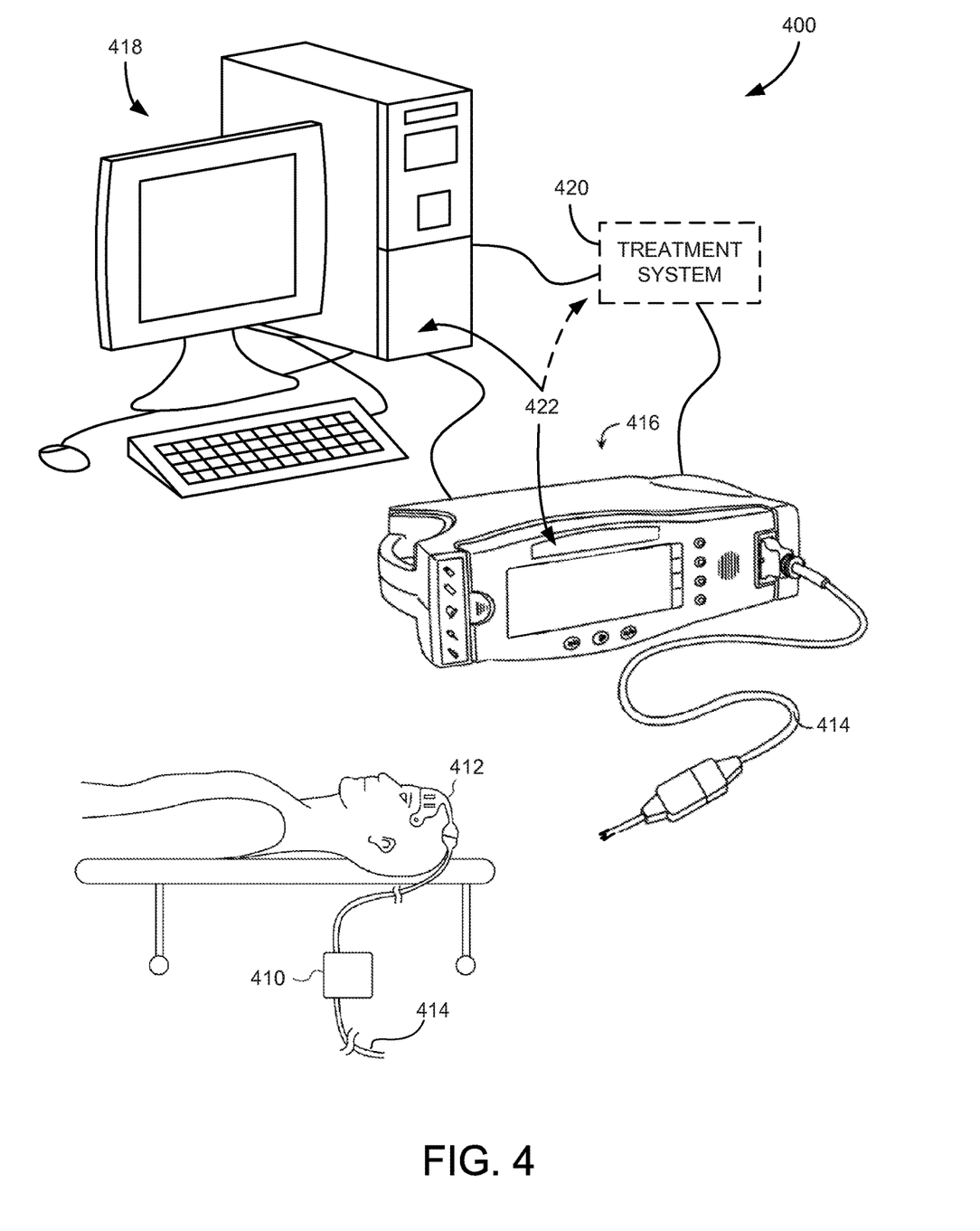
FIG. 4 is an example physiological monitoring system, in accordance with aspects of the present disclosure.

Specifically now referring to FIG. 4, an example system 400 in accordance with the present disclosure is illustrated, for use in monitoring and/or controlling a state of a subject during a medical procedure, or as result of an injury, pathology or other condition. In some aspects, the system 400 could be used to guide or control, as non-limiting examples, medically-induced coma, anesthesia, or sedation. In other aspects, the system 400 could be used to guide or control medically-induced hypothermia, for instance during hypothermia treatment after cardiac arrest, or during cardiac surgery.

The system 400 includes a subject monitoring device 412 that may include multiple physiological sensors, such as EEG sensors. However, it is contemplated that the subject monitoring device 412 may incorporate other sensors including blood oxygenation sensors, temperature sensors, acoustic respiration monitoring sensors, galvanic skin response sensors and so forth.

The subject monitoring device 412 is connected via a cable 414 to communicate with a monitoring system 416, which may be a portable system or device, and provides input of physiological data acquired from a subject to the monitoring system 416. Alternatively, the cable 414 and similar connections can be replaced by wireless connections between components. The monitoring system 416 may be configured to receive raw signals acquired by the sensors and assemble, and even display, the raw or processed signals or information derived therefrom.

As illustrated in FIG. 4, the monitoring system 416 may be further connected to a dedicated analysis system 418. In some aspects, the analysis system 418 may receive the data from the monitoring system 416, and perform a phase-amplitude coupling analysis to identify brain states of the subject, such as levels of consciousness, and generate a report, for example, as a printed report or, preferably, a real-time display of signature information and identified states. In some aspects, the subject monitoring device 412 may be in communication with a portable processing system 410, for instance, as described with reference to FIG. 2, which may be configured for perform any number of processing steps, such as identifying and/or relaying information relating to brain states of a subject. Although shown as separate systems in FIG. 4, it is also contemplated that components and/or functionalities monitoring system 418 and analysis system 418 and system 400 may be combined or integrated.

In some configurations, the system 400 may also include a treatment system 420. The treatment system 420 may be coupled to the analysis system 418 and monitoring system 416, such that the system 400 forms a closed-loop monitoring and control system. Such a closed-loop monitoring and control system may capable of a wide range of operation, and may include a user interface 422, or user input, to allow a user to configure the closed-loop monitoring and control system, receive feedback from the closed-loop monitoring and control system, and, if needed reconfigure and/or override the closed-loop monitoring and control system.

In some configurations, the treatment system 420 may include a drug delivery system not only able to control the administration of anesthetic compounds for the purpose of placing the subject in a state of reduced consciousness influenced by the anesthetic compounds, such as general anesthesia or sedation, but can also implement and reflect systems and methods for bringing a subject to and from a state of greater or lesser consciousness. In other configurations the treatment system 420 may include a hypothermia treatment system. Other treatments may be administered or facilitated by the treatment system 420 as well.

The above-described systems and methods may be further understood by way of example. This example is offered for illustrative purposes only, and is not intended to limit the scope of the present invention in any way. Indeed, various modifications of the invention in addition to those shown and described herein will become apparent to those skilled in the art from the foregoing description and the following examples and fall within the scope of the appended claims. For example, specific examples of brain states, medical conditions, levels of anesthesia or sedation and so on, in association with specific drugs and medical procedures are provided, although it will be appreciated that other drugs, doses, states, conditions and procedures, may be considered within the scope of the present invention. Furthermore, examples are given with respect to specific indicators related to brain states, although it may be understood that other indicators and combinations thereof may also be considered within the scope of the present invention. Likewise, specific process parameters and methods are recited that may be altered or varied based on variables such as signal amplitude, phase, frequency, duration and so forth.

EXAMPLE

Ten healthy volunteers (5 male) were induced and allowed recovery from general anesthesia using the intravenous anesthetic propofol (2,6 di-isopropyl-phenol). Propofol concentration increased in steps from 0 to 5 mcg/ml every 14 min, followed by gradual reduction (see FIG. 1a). A 64 channel EEG data was acquired using a BrainVision MRI Plus system (BrainAmp MRPlus, Brain-Products) with sampling rate 5 kHz, resolution density (see FIG. 1c) was computed using a multitaper method (window 0.5 microV least significant bit, and bandwidth 0.016-1000 Hz. Galvanic skin response and plethysmography (PowerLab; AD Instruments) was also recorded. Electrodes, amplifiers, and filter settings provided accurate and unbiased recording of the entire frequency range analyzed in this study (0.1-50 Hz). A Bayesian method was used to estimate the time-varying probability of response (see FIG. 1b). The time of loss of consciousness (LOC), tLOC, and return of consciousness (ROC), tROC, were defined as the first and last times at which the median response probability was less than 0.05.

EEG data were re-referenced using a Laplacian montage by subtracting the mean of each channel's nearest neighbors. The Laplacian montage improves spatial localization of focal sources but attenuates EEG components with low spatial frequencies. Because these components tend to have low temporal frequencies, it was also found to attenuate low temporal frequencies. It was verified that the reference choice had a minor impact on measurement of phase-amplitude coupling by repeating the analysis using the average of mastoid electrodes as a reference. Raw signals, $x_{lo}(t)$, were first smoothed using an anti-aliasing filter and down-sampled to 250 Hz. Ultra-low-frequency drift was removed by subtracting a piecewise quadratic spline fit to the signal with knots every 15 s. Bad channels were rejected by visual inspection. A conservative procedure was adopted to remove low-frequency, large amplitude EEG artifacts caused by movements while subjects were awake. The low-frequency signal, $x_{lo}(t)$ was extracted by applying a band-pass filter (0.2-6 Hz), down-sampling to 5 Hz, and then applying a medial filter (window size 30 s) to $|x_{lo}(t)|$. Artifacts were defined as any time points for which $|x_{lo}(t)|$ was at least 10-fold greater than this local threshold. Data within ±5 s of any artifact on each channel was excluded. Power spectral density (see FIG. 1c) was computed using a multitaper method (2 sec window size and 3 tapers).

In addition, eight subjects (5 male) with epilepsy intractable to medication were implanted with intracranial subdural electrocorticography ("ECoG") electrodes for clinical monitoring (1 cm spacing, AdTech). Electrode placement was determined by clinical criteria, and covered regions within temporal, frontal, and parietal cortices (7 of 8 patients in the left hemisphere). Recordings were collected during surgery for electrode explanation. Anesthesia was administered as a bolus of propofol according to standard clinical protocol based on the anesthesiologist's clinical judgment. ECOoG data was sampled at 500 Hz with a single reference placed facing the dura in the posterior parietal region. After visual rejection of bad channels, the same analysis of EEG data was applied, as described above. Individual MR and CT images were used to localize electrodes with respect to the cortical surface. These locations were mapped to an average reference brain and combined across subjects for display.

Figure 5:
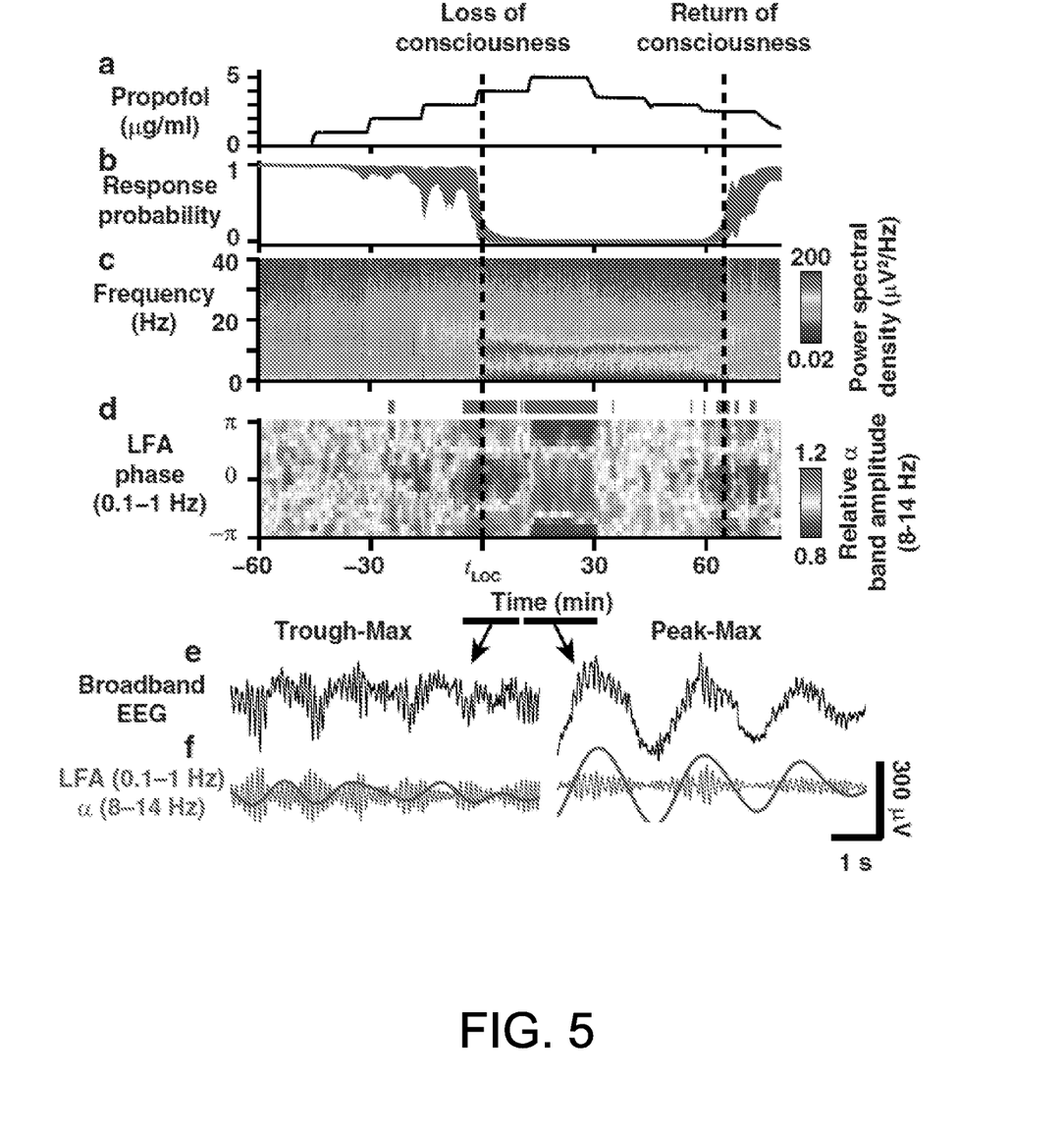
FIG. 5 is a graphical illustration showing a phase-coupling transition during general anesthesia using profopol.

Results obtained indicate that the general anesthetic drug propofol evokes distinct unconscious brain states with opposite patterns of phase-amplitude coupling and unique source distributions, as illustrated in FIG. 5. Specifically, during controlled administration of profol (FIG. 5A) power spectral analysis showed that β power (12-20 Hz) increases at subanesthetic concentrations before loss of consciousness ("LOC"), followed by a sustained increase in low frequency activity ("LFA") (0.1-1 Hz), and a frontally organized α rhythm (8-14 Hz) throughout the period of unconsciousness (FIG. 5C). By analyzing cross-frequency phase-amplitude coupling, it was discovered that the frontal α rhythm waxes and wanes at specific phases of the LFA during unconsciousness (FIG. 1D; gray bars). This coupling is also visible in raw EEG traces (FIGS. 5E and 5E).

Two distinct patterns of phase-amplitude coupling were observed during the unconscious period. At the threshold propofol concentration for LOC, $c_{LOC}$, α amplitude was largest during the surface-negative phase of the LFA (trough-max). After an increase in propofol concentration, the phase-amplitude relationship abruptly reversed, with maximum α amplitude at the surface-positive phase of the LFA (peak-max). The transition between trough- and peak-max coupling occurred within a few minutes, after which the peak-max pattern remained until the propofol concentration was reduced. The change in phase-amplitude coupling did not coincide with the major increase in low-frequency EEG power, which occurred at LOC (FIG. 5C). This highlights the need for cross-frequency analysis to detect the shift in network dynamics.

Figure 6A:
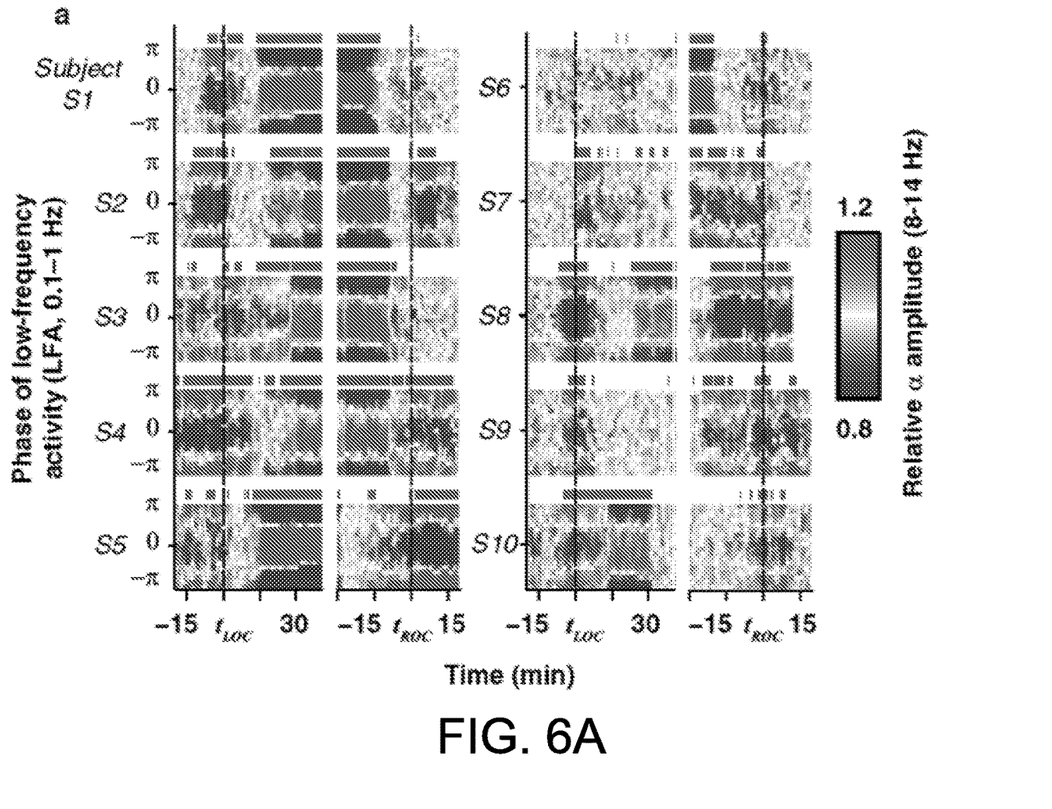
FIG. 6A are graphical illustrations showing phase-amplitude couplings for a number of subjects during anesthesia.
Figure 6B:
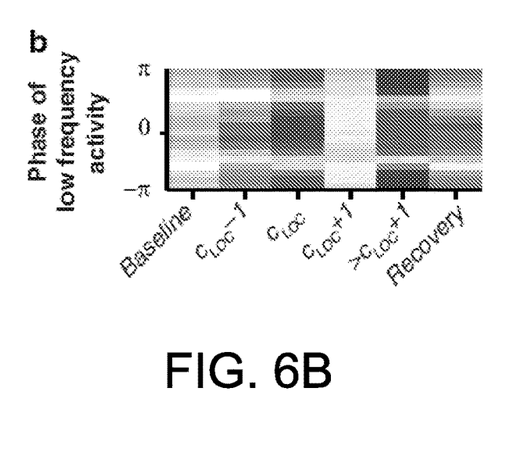
FIG. 6B is a graphical illustration showing a mean coupling pattern across a population of subjects at various drug concentrations.
Figure 6C:
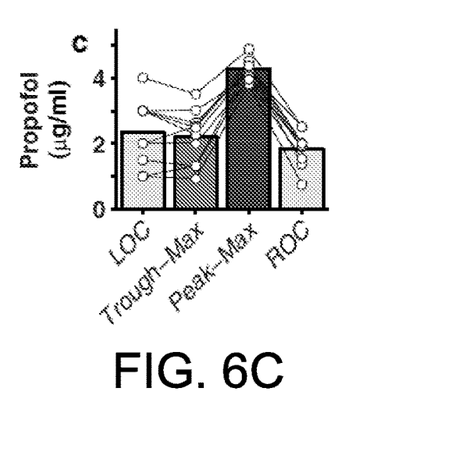
FIG. 6C is a graphical illustration showing mean concentration of propofol at loss of consciousness, recovery of consciousness, and during trough-max and peak-max epochs.

All of study subjects (n=10) showed significant trough-max coupling during the transition to and/or recovery from un-consciousness, and eight showed significant peak-max coupling at the highest propofol concentrations (5 microg/ml) (FIG. 6A-C). Overall, coupling was significant at frontal locations during 67% of unconscious epochs; only 11% were significant before propofol administration. The median modulation index ("MI"), a measure of coupling strength, doubled from $6\times10^{-3}$ bits at baseline to $12\times10^{-3}$ bits after LOC (p<10-3, Mann-Whitney U test).

Figure 6D:
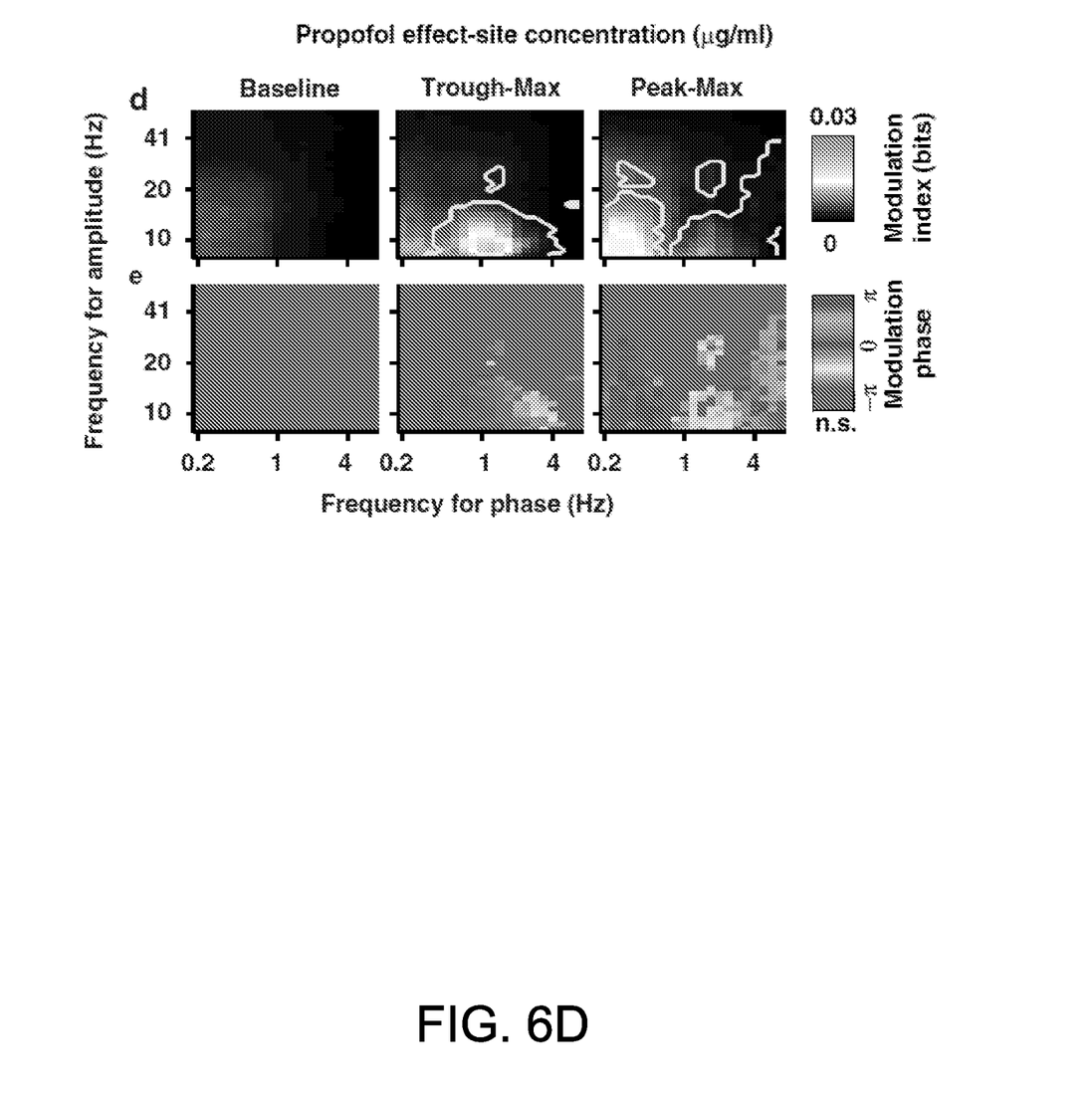
FIG. 6D is a graphical illustration showing median modulation index and modulation phase across a population of subjects as a function of the center of the frequency based used for phase and amplitude.

The frequency dependence of phase-amplitude coupling was also examined Although significant phase-amplitude coupling was observed in some subjects while they were awake before LOC (FIG. 5A), overall coupling before propofol administration was not consistent across subjects for any of the frequencies tested (0.2-50 Hz; FIG. 6D-E). After LOC, phase-amplitude coupling was concentrated within the LFA and α bands. Trough-max coupling linked LFA and δ phase (0.4-4 Hz) with and α low β amplitude (8.3-17 Hz). During peak-max epochs, separate patterns of coupling were found between α amplitude and the LFA (0.1-1 Hz) and δ (1-4 Hz) bands. α amplitude being the highest at the peaks of the LFA, whereas coupling to the δ band peaked about $-\pi/2$, (FIG. 6D)

Figure 7:
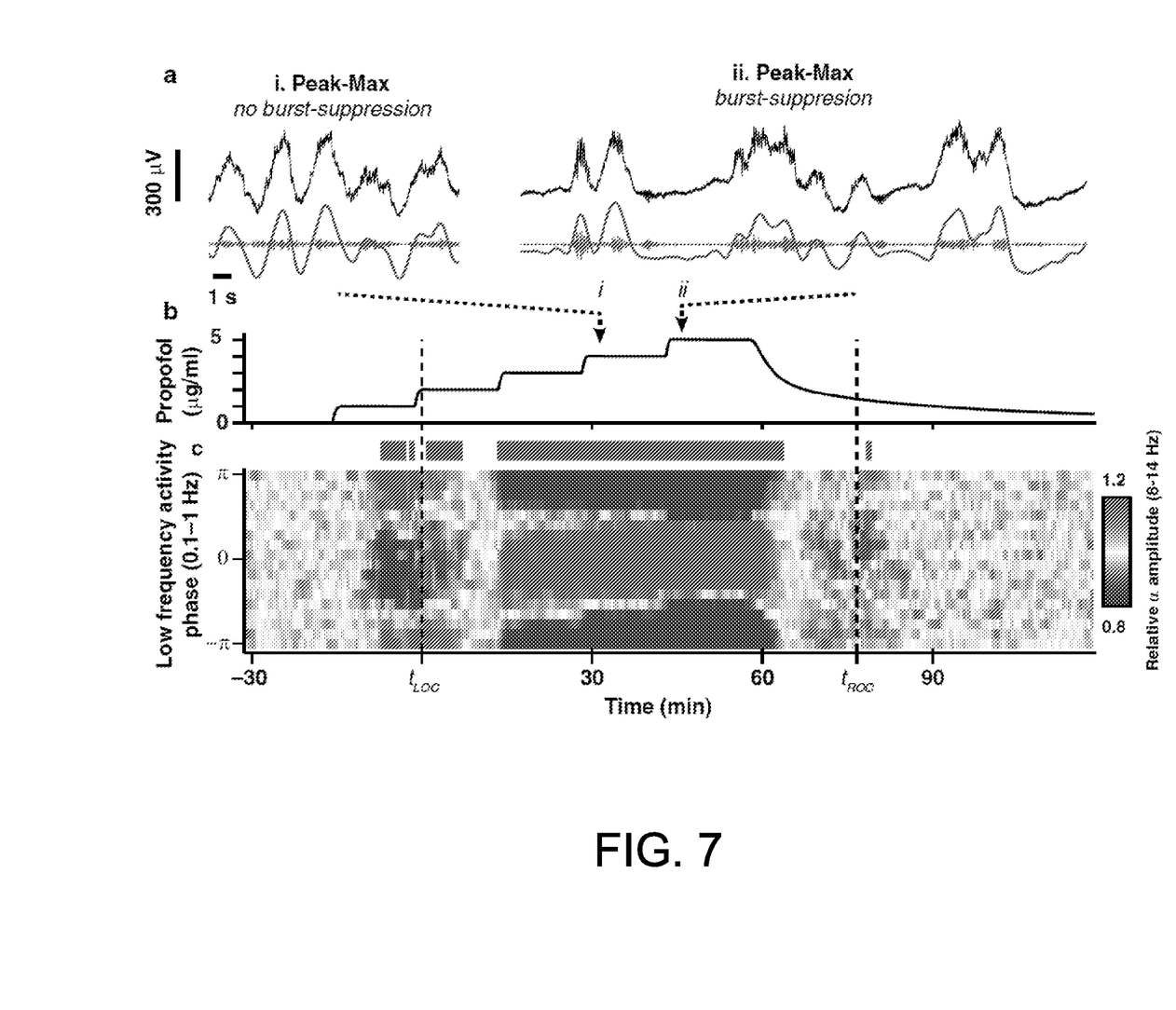
FIG. 7 is a graphical illustration showing that peak-max coupling is not identical with burst suppression brain state.

Profound unconsciousness during general anesthesia, coma, and hypothermia can evoke a burst suppression pattern in which high-frequency activity alternates with isoelectric periods. Burst suppression is a distinct state from sleep slow waves and slow oscillations during general anesthesia, which are more regular and alternate at a faster rate. In the present study, 4 of 10 subjects entered a state of burst suppression at the highest propofol concentration. These subjects exhibited peak-max coupling during both burst suppression and non-burst suppression epochs (FIG. 7). Peak-max coupling is therefore not simply a consequence of burst suppression but in stead represents a network state, which can occur at lower anesthetic drug doses, and also during the active burst period during burst suppression.

Figure 8:
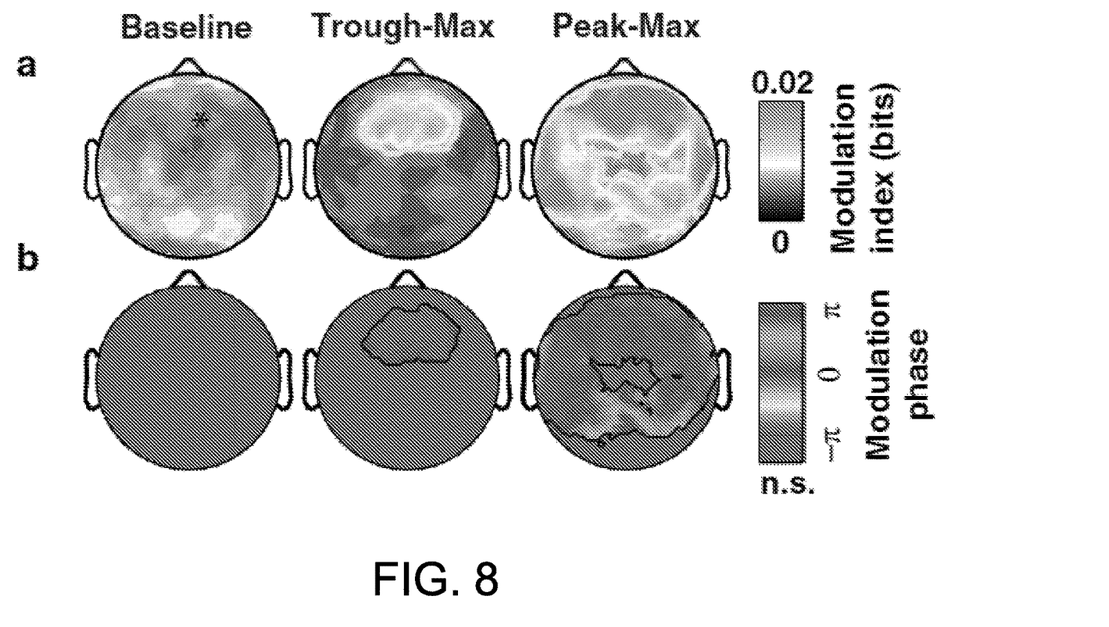
FIG. 8 is a graphical illustration showing spatial distribution of phase-amplitude coupling at baseline, trough-max and peak-max epochs.
Figure 9:
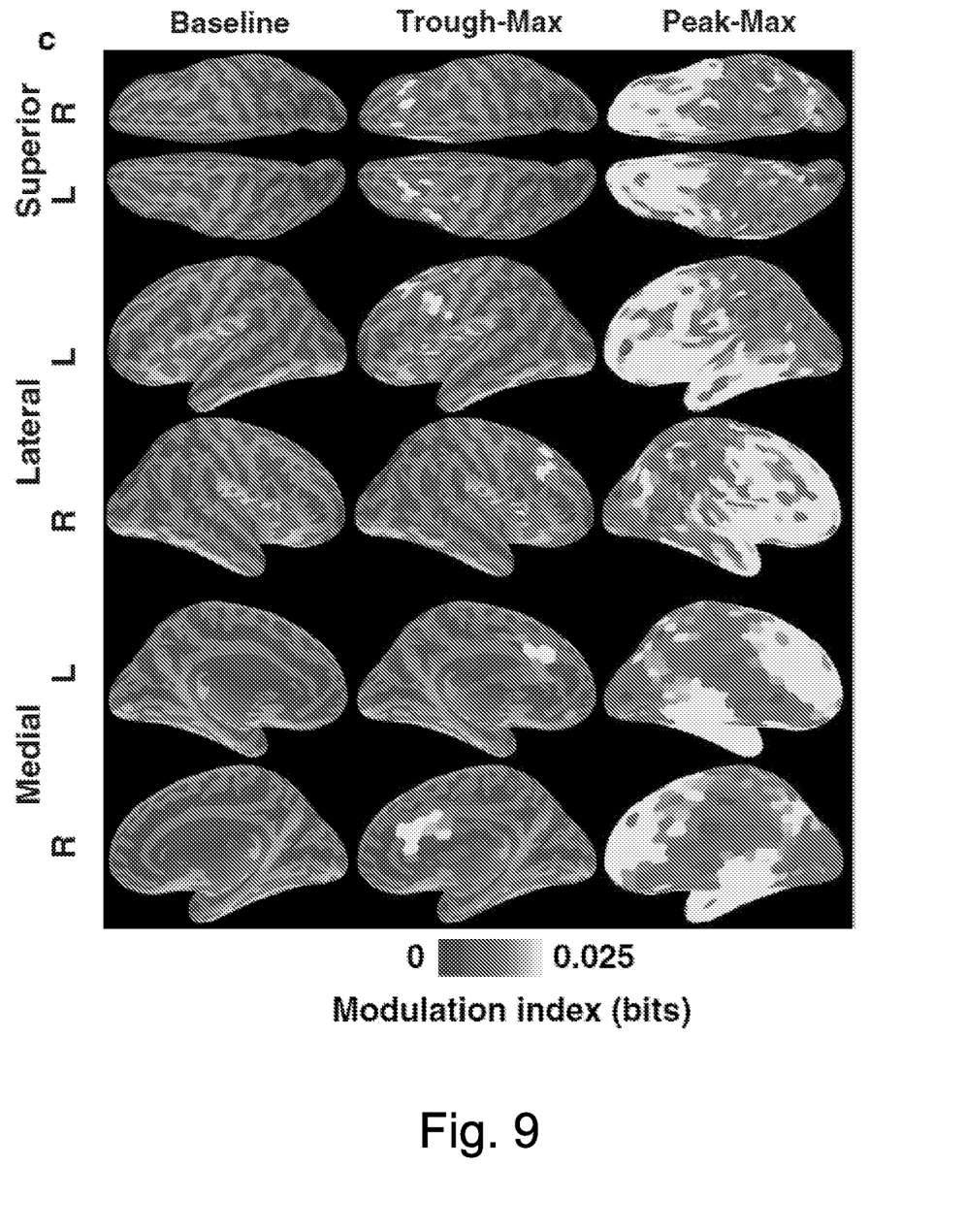
FIG. 9 is a graphical illustration showing average modulation index at cortical patches estimated by source localization analysis of EEG signals.

Peak- and trough-max coupling had distinct spatial profiles over the scalp and across cortical regions. Traditional frequency-band analysis has identified the occipital-to-frontal shift in low-frequency (<40 Hz) scalp EEG power as a hallmark of general anesthesia. During the transition to unconsciousness, herein it was found that trough-max coupling of α amplitude with LFA phase was likewise concentrated at frontal electrodes (FIG. 8). However, peak-max coupling dominated activity throughout frontal, temporal, and posterocentral regions. Each subject's anatomical MRI was used to reconstruct cranial tissue surfaces and perform biophysical model-based source localization using a minimum norm estimation algorithm (FIG. 9). This procedure is biased toward distributed cortical sources, so these results represent a conservative estimate of localization. Significant trough-max coupling in anterior cingulate and frontal cortices bilaterally was found, whereas peak-max coupling extended throughout much of the cortex and was strongest in frontal and temporal lobes.

Figure 10:
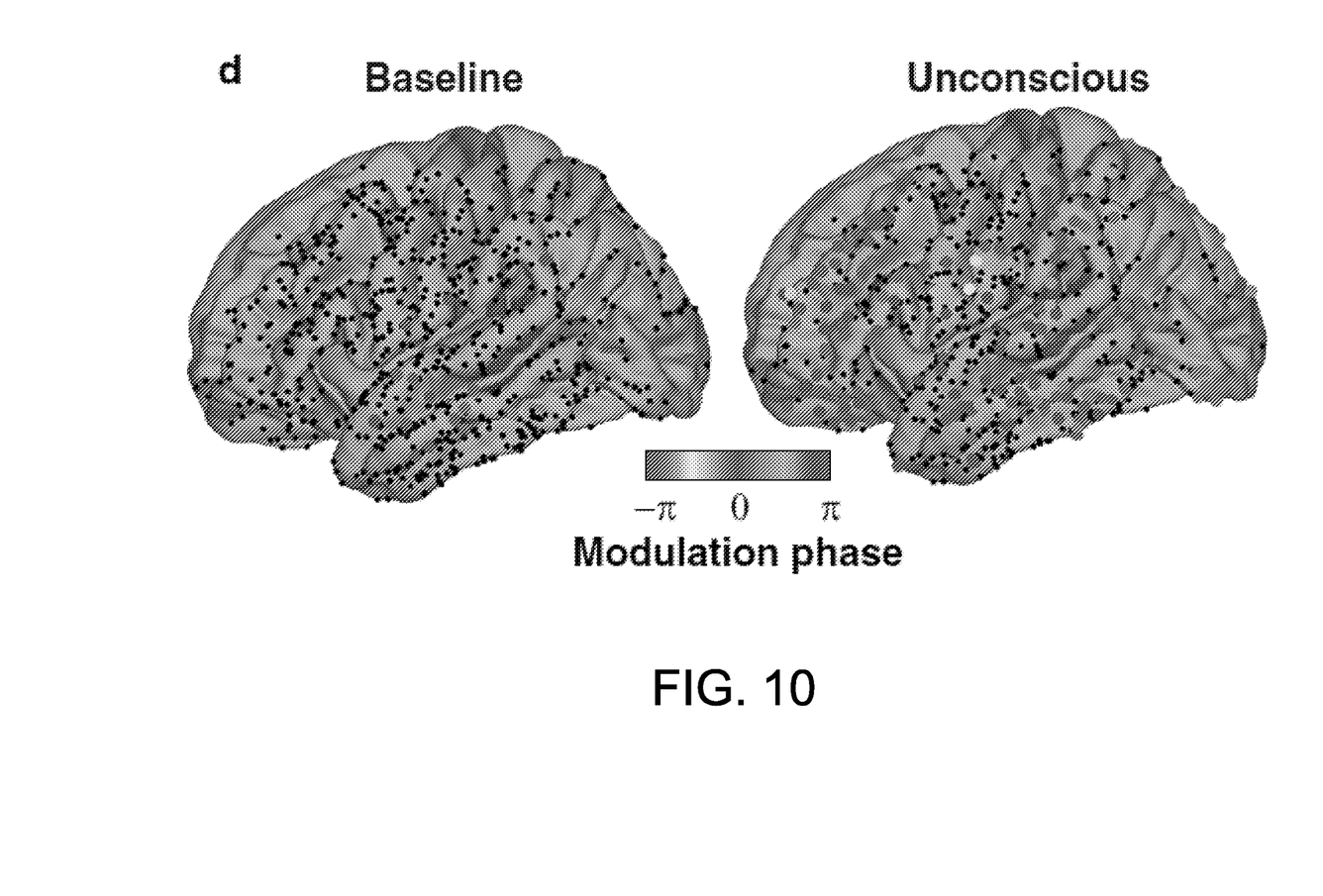
FIG. 10 is a graphical illustration of locations of intracranial cortical surface electrodes mapped to an average cortical surface.

To directly examine the cortical sources of phase-amplitude coupled activity with high spatial resolution, intracranial ECoG data was recorded using subdural electrode grids in 8 epilepsy subjects during induction of general anesthesia with propofol (605 total electrodes). After LOC, significant coupling appeared in frontal, occipital, and temporal cortices (FIG. 10). The sign of the referential ECoG varies depending on the geometry of local sources, resulting in a bimodal distribution of coupling phase concentrated at 0 and $\pi$ (FIG. 10).

Data herein that propofol consistently evokes two distinct cortical states with opposite phase-amplitude coupling. These EEG patterns appear in a stereotyped progression during the induction of and recovery from unconsciousness. In contrast with phase-amplitude coupling observed during waking and sleep states, the patterns observed herein critically involve the frontal α rhythm, which is a hallmark of general anesthesia. Peak-max coupling resembles the well-studied slow oscillation, in which scalp-positive waves are associated with transient activated cortical UP/ON states showing increased broadband EEG, local field potential power, and multiunit activity, whereas scalp-negative waves are associated with quiescent DOWN/OFF states. It was found that peak-max coupling does not require a burst suppression activity pattern. Rather, peak-max coupling may be a general signature of unconsciousness in the cortex that precedes the onset of burst suppression.

The trough-max pattern parallels reports of increased cortical excitability and attention during the surface-negative phase of slow cortical potentials. This pattern is localized in anterior cingulate and frontal cortices, the most rostral portion of an ascending arousal system, including brainstem, thalamic, and cortical networks that becomes more metabolically active during emergence from propofol-induced unconsciousness. Activity in anterior cingulate and frontal cortices also covaries with spontaneous fluctuations in internal awareness; the trough-max pattern might therefore be associated with propofol-induced changes in circuits mediating internal awareness.

The transition identified herein in cortical dynamics shows that unconsciousness during propofol general anesthesia is not a unitary brain state. Instead, propofol evokes at least two distinct states with opposite patterns of cross-frequency phase-amplitude coupling that engage different cortical networks. The fact that these opposing modulation patterns are mutually exclusive, with distinct spatial distributions, suggests that alternation between widespread cortical ON and OFF states during peak-max coupling begins only after disruption of the frontal trough-max pattern. These objective EEG landmarks enable reliable interpretation of the physiology and functional significance of cortical activity during unconsciousness.

FIGS. 5, 6A, and 6B show that the state of phase-amplitude modulation reflects varying levels of unconsciousness with increasing or decreasing anesthetic drug dose. These figures show that with increasing drug levels, and decreasing probability of response, the phase amplitude modulation state changes from trough-max to peak-max, passing through an intermediate state where neither troughnor peak-max modulation are present. FIGS. 8 and 9 show that the trough- and peak-max modulation patterns reflect activity within distinct neural circuits, and thus reflect distinct states of unconsciousness with different properties that may be clinically desired or clinically disadvantageous, depending on the context. This information could be used to monitor and manage sedation and general anesthesia by clinicians as well as by automated control algorithms. For instance, if an anesthesiologist observed that the patient transitioned into trough-max modulation from a deeper state (peak-max or the intermediate state between trough- and peak-max), it would indicate that the patient was recovering consciousness. The trough-max state is localized to anterior cingulate and frontal cortices, which imply that a degree of internal consciousness may be present in patients displaying this pattern of modulation. Such patients in a trough-max state could be aroused to responsiveness by external stimuli. Consequently, during surgery under general anesthesia, the trough-max state might reflect an inadequate state of impaired consciousness for the clinical situation. In contrast, for surgical or medical procedures requiring only sedation or monitored anesthesia care, where it might be desirable to have the patient respond to verbal or tactile stimuli and regain consciousness quickly, the trough-max state could reflect a clinically-appropriate state of impaired consciousness.

The peak-max state, as well as the intermediate state between trough- and peak-max, reflects a deeper level of impaired consciousness, in which it may not be possible to be aroused to responsiveness by external stimuli. Such brain states might therefore be highly appropriate clinically for surgery under general anesthesia where patients must remain unconscious or unaware. Because the peak-max state precedes burst suppression, it could be used as an indicator to prevent over-administration of anesthetics into a burst suppression state.

A similar rationale could be employed to administer sedation to patients in the intensive care unit. The trough-max modulation signal could be used to establish a state of sedation where patients are unconscious but can be aroused to consciousness with verbal or tactile stimuli. The state in-between trough- and peak-max, as well as peak-max itself, could be an indicator of either deep sedation, or sedation that is too deep if lighter sedation is clinically indicated.

Clinical criteria as described above could be implemented in automated control algorithms to maintain brain states indicated by phase-amplitude modulation during general anesthesia or sedation.

The frequency distribution for phase-amplitude modulation, as represented in FIG. 6D, for instance, could be used to help identify different drugs used in anesthesia or other applications. For instance, different drugs may show different frequencies for phase, or different frequencies for amplitude, over which phase-amplitude modulation is present. Moreover, the specific phase relationship, indicated by the modulation phase in FIG. 6D, may differ according to drug. In anesthesia and intensive care applications where multiple drugs are being used, this ability to distinguish between different drugs could be used to help identify which drug in a given combination is working in a dominant fashion. Such a determination could then be used to help adjust the combination of drugs begin administered, or guide future administration of drugs given the kinetics of the drug presently being administered.

The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A system for monitoring consciousness of a subject experiencing anesthesia, the system comprising:
   a plurality of sensors configured to be placed about the subject and configured to acquire electroencephalogram ("EEG") data therefrom while the subject is receiving anesthesia;
   at least one processor configured to:
   receive the EEG data from the plurality of sensors;
   perform a phase-amplitude coupling analysis using the received EEG data to determine a phase-amplitude frequency distribution;
   identify a state of consciousness of the subject using the determined phase-amplitude frequency distribution;
   generate a report indicative of the state of consciousness of the subject; and
   determine a polarity of a phase-coupling modulation associated with the received EEG data.

2. The system of claim 1, wherein the processor is further configured to determine a baseline phase-amplitude frequency distribution.

3. The system of claim 2, wherein identifying the state of consciousness of the subject further comprises comparing the phase-amplitude frequency distribution to the baseline phase-amplitude frequency distribution.

4. The system of claim 1, wherein identifying the state of consciousness of the subject further comprises comparing the polarity of the phase-coupling modulation to a baseline polarity of the phase-coupling modulation.

5. The system of claim 1, wherein the at least one processor is further configured to determine a spatial distribution of phase-amplitude coupling using the received EEG data.

6. The system of claim 1, wherein identifying the state of consciousness of the subject further comprises correlating a dose of anesthesia with the determined phase-amplitude frequency distribution.

7. The system of claim 1, wherein identifying the state of consciousness of the subject further comprises determining trough-max and peak-max modulation patterns.

* * * * *

UNITED STATES PATENT AND TRADEMARK OFFICE
CERTIFICATE OF CORRECTION

| | |
|---|---|
| PATENT NO. | : 10,674,956 B2 |
| APPLICATION NO. | : 15/111002 |
| DATED | : June 9, 2020 |
| INVENTOR(S) | : Patrick L. Purdon et al. |

It is certified that error appears in the above-identified patent and that said Letters Patent is hereby corrected as shown below:

In the Specification

Please insert the following after the first paragraph in Column 1, Line 6:
--STATEMENT REGARDING FEDERALLY SPONSORED RESEARCH
This invention was made with government support under OD006454 awarded by the National Institutes of Health. The government has certain rights in the invention.--.

Signed and Sealed this
Ninth Day of May, 2023

Katherine Kelly Vidal
*Director of the United States Patent and Trademark Office*